United States Patent
Foser

[11] Patent Number: 5,733,125
[45] Date of Patent: Mar. 31, 1998

[54] DENTURE

[75] Inventor: Hans-Peter Foser, Balzers, Liechtenstein

[73] Assignee: Ivoclar AG, Liechtenstein

[21] Appl. No.: 647,197

[22] Filed: Mar. 11, 1996

[30] Foreign Application Priority Data

Mar. 10, 1995 [DE] Germany ............ 195 08 762.3

[51] Int. Cl.$^6$ ............................................. A61C 13/08
[52] U.S. Cl. ......................................................... 433/197
[58] Field of Search .......................... 433/197, 202.1, 433/204, 212.1, 218

[56] References Cited

U.S. PATENT DOCUMENTS

| 1,665,357 | 4/1928 | Gysi. |
| 1,677,662 | 7/1928 | Sprinkle ............ 433/197 |
| 3,060,576 | 10/1962 | Hass ................ 433/197 |
| 3,755,898 | 9/1973 | Warren. |
| 4,208,794 | 6/1980 | Gerber ............. 433/197 |
| 4,445,863 | 5/1984 | Lang et al.. |

FOREIGN PATENT DOCUMENTS

| 405601 | 7/1966 | Switzerland. |
| 130870 | 8/1919 | United Kingdom. |

Primary Examiner—Cary E. O'Connor
Attorney, Agent, or Firm—John C. Thompson

[57] ABSTRACT

In the case of a denture made of pre-fabricated teeth, that exhibits molars and pre-molars for each jaw, upper and lower, at least on the upper molars at the lingual position, an incising ridge (24) is provided. The incising ridge is intended, in the occlusion position, to engage the masticatory surface (18) of the antagonist of the lower jaw (14) in each case. The masticatory surface (18) exhibits a sulcus (45) with at least some areas of convex arcuate projection (20, 22) by means of which the antagonist (14) may be centered in tripodized incuspidation on the incising ridge (24).

15 Claims, 3 Drawing Sheets

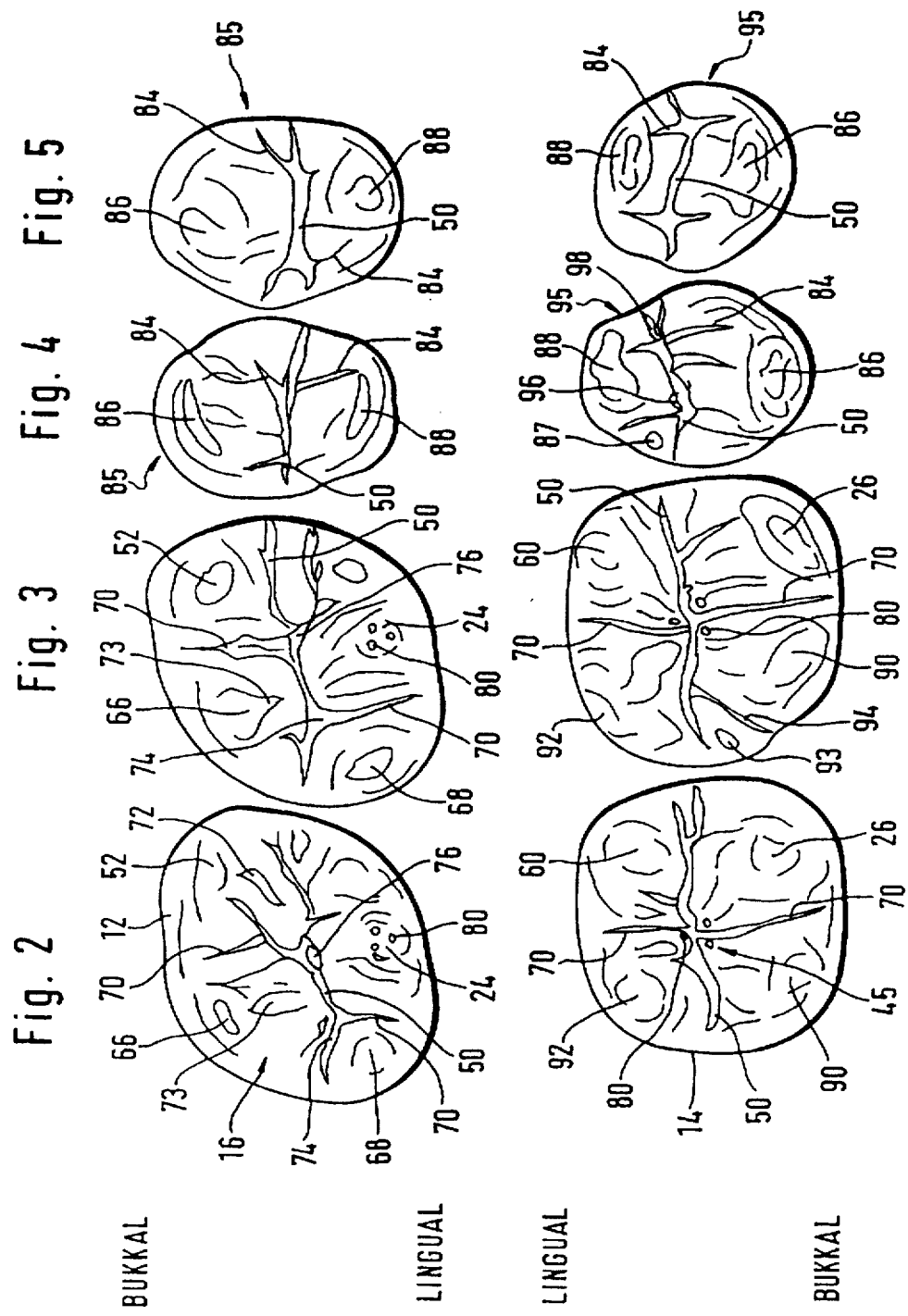

ic. The fundamental structure of the teeth according to the invention, with molars and/or pre-molars in the upper jaw, which, at their lingual position, exhibit an incising ridge which, in occlusion position, is intended to engage the masticating surface of its lower jaw antagonist, makes such combinations possible. For such cases, it is particularly suitable to make the masticating surface of the antagonist of the natural tooth.

DENTURE

TECHNICAL FIELD

The present invention relates to a set of teeth or denture made of pre-fabricated teeth with molars and/or pre-molars for each upper and lower jaw, in which at least the upper jaw molars at lingual position exhibit an incising ridge, each of which, ion occulsion position, is intended to engage the masticating surface of its lower jaw antagonist.

BACKGROUND OF THE INVENTION

A denture is known from the Swiss patent CH-PS405 601. The masticating effectiveness of the teeth is relatively good if a grinding function stands in the foreground, due to the fact that they work in accordance with the mortar and pestle principle. The masticating effect decreases to a marked degree, however, if fibrous substances, such as meat that exhibits fibrous orientation, or vegetables of the same type, are to be reduced in size between the pre-fabricated teeth according to CH-PS-405 601 as a result of mastication. In the case of the previously-known denture, a motorial rest is said to be created by virtue of the fact that the radii of curvature in the case of convex surfaces that encounter one another are selected in such a manner as to be considerably smaller than in the case of concave surfaces. Such an embodiment, however, does not preclude the possibility, for example, that the ridge of the upper jaw might find its way to the mesio-distal edge of a lower jaw, which is unfavorable from the standpoint of the situation of the load that is imposed upon the tooth, but it also diminishes the motorial rest.

It is known that the lower jaw, in the process of mastication, passes through a special curve extending in space, which is designated the mastication loop. With reference to the molars of the lower jaw for example, the mastication loop, shortly before occlusion, describes an oblique motion, in both the lingual or buccal direction, as well as in the distal direction of the lower jaw, toward the upper jaw. Due to this shift, the antagonists regularly come into contact, initially on their edges, and, in point of fact, regularly on that side on which less food is reduced in size, on the so-called balancing side. In the case of natural teeth, the inclination of the ridge is such that the balancing side also draws the working side as a result of the workings of the masseter muscle and medial pterygoideus muscle into so-called balanced occlusion. Support on the balancing side has the advantage that the working side renders a great mastication effect possible using relatively little muscular strength, according to the principle of the one-armed lever.

The denture that is known from CH-PS-405 601 does not do justice to this principle, or does so to only a slight degree. As a result of the concave embodiment with relatively large radii, no, or only slight, guiding function occurs on the balancing side. In addition, it may even happen that the incising ridge makes its way lingually with respect to the lingual ridge of the antagonist, and faulty occlusion results.

Natural teeth are subjected, as they approach the occlusion position, to a front-eye tooth guidance, which permits, due to the good guiding power of natural eye teeth, definite occlusion positioning. It is known how to realize this concept of front-eye tooth guidance, even in the case of artificial teeth. In the case of a full plate, however, the result, when doing so, is comparatively great lateral forces that are introduced into the anterior region of the plate, which forces may be absorbed between the jaw and the plate to no more than an inadequate degree. Accordingly, the plate glides in a horizontal plane, which can cause pain and be damaging to tissues. In the case of a partial plate, however, it would be desirable to be able to realize this concept as well, so that the dentures may be used in either full or partial plates.

Furthermore, dentures are known from the U.S. Pat. No 3,755,898 that combine both convex surfaces of lesser radii with concave surfaces of greater radii. In addition, a multitude of transverse sulci, each of which is closed on one side and open on the lingual or buccal end, and by means of which, nutritive chyme that has been reduced in size is to be expressed. Such a denture exhibits, fundamentally, no incising ridge, but rather a kind of grinding bar on the upper jaw that extends in the mesio-distal direction.

This form of tooth does not, however, permit the desired motorial rest and cannot follow the mesio-distal movement component toward the end of the mastication loop by approximating the occlusion position.

In addition, comparatively sharp edges are unfavorable if ceramic teeth are combined with natural teeth. The ceramic teeth are regularly markedly harder than the natural teeth, so that undesired wear of the natural teeth occurs. Therefore, the solution known from U.S. Pat. No. 3,755,898 is basically well-suited only for plastic teeth at best.

By contrast, the underlying task of the invention is to create a denture, which lends itself well to both full and partial plates, which renders the realization of various occlusion concepts possible, and one that is, in spite of industrial pre-fabrication, and improved mastication effect, universally applicable.

This task is resolved according to the invention by making a denture of pre-fabricated teeth with molars and/or pre-molars for each upper and lower jaw, in which at least the upper jaw molars at lingual position exhibit an incising ridge, each of which, in occlusion position, is intended to engage the masticating surface of its lower jaw antagonist in each case, characterized by the fact that the masticating surface of the antagonist exhibits a sulcus with at least some convex arcuate areas, by means of which the antagonist may be centered in multiple contact intercuspidation at the incising ridge.

It is particularly favorable that, using the centering in multiple contact intercuspidation according to the invention, particularly in tripodized intercuspidation, improved masticatory effects may be achieved with lesser masticatory power. The balancing side, in the case of the dentures according to the invention finds its way, without further ado, into the maximal occlusion position, so that the masticatory effect can then be maximized on the working side via the masseter muscle. In the process, because of the convex arcuate occlusion surfaces, it is possible to reduce even fibrous foods quite readily, without having, for example, to realize an incisor-like concept for the pre-molars in order to shift the cutting function to the latter.

And yet, even in the course of a normal bite, the introduction of power is optimized. It is possible to keep the support, briefly before maximum power is applied, that is, briefly before the food is finally divided, at at least two points of contact, or points of approach, preferably three points of contact or approach, which are arranged in a substantially symmetrical manner. The force vectors that are introduced are then neutralized with reference to the horizontal plane, and it is only necessary to make certain that the central point is oriented so as to be about centrally located with respect to the ridge of the lower and upper jaw.

According to the invention, the dentures may also be used for partial plates, that is, with a natural tooth as the antagonist. In this process, it is possible to exploit, in a particularly favorable manner, the fact that the centering according to the invention is also possible when natural teeth are the antagonists. By reducing the contact surfaces to the three contact points, the masticatory effect is particularly good, without precluding a grinding function. In this regard, it is particularly favorable that the invention open the possibility of adding to the at least partially convex arcuate areas, concave arcuate areas, which permit an inter-coronal free space. In this way, it is possible to realize the mortar and pestle principle, and it will be understood that the continuation can occur in both mesio-distal or bucco-lingual direction, and it may not necessarily occur, in each case, in the direction of a ridge projecting from a central ridge, but it may also occur, for example, in the direction of a transverse sulcus.

According to another advantageous embodiment, it is possible to render at least two, preferably three or more, contact points between the incising ridge and the antagonist possible by a contact between a buccal ridge of the lower jaw and the buccal side of the central fossa of the upper jaw. In this way, the introduction of force is shifted toward the lingual, which is favorable for the normal bite, and additional guidance of the lower jaw in the lingual direction occurs, which also prevents a cross bite from occurring unintentionally.

In conjunction with the guidance of the teeth into the occlusion position via the balancing side, it is particularly favorable if the distance between the central fossa and a labial ridge of the molars is smaller than the distance between the central fossa and the buccal ridge of the corresponding antagonist of the lower jaw. Then, in practical terms, a very wide guidance area is available on the upper jaw for the guidance of the balancing side into intercuspidation.

An asymmetry and a transversal or sagittal shifting of the ridge and the arcuate projections is favorable if the task at hand is to optimize the contact points of the teeth.

It is particularly favorable if, in each case, a defined width of masticating surface between approximately 5.7 and 7.0 mm for the pre-molars of the lower jaw, and between, for example, 5.9 and 6.8 mm for the molars of the lower jaw, and between approximately 4.8 and 7.3 mm for the pre-molars of the upper jaw, and between, for example, 6.2 and 7.8 mm for the molars of the upper jaw, is provided. By these means, a better distribution of the burden is obtained in comparison with the known, frequently quite narrow, teeth of the lower jaw, such that, surprisingly, when precisely this width of tooth is present, optimal masticatory function is extant, regardless of the size of the denture, which may, in principle, be provided in a plurality of sizes, for example, in five gradations of size, each of which differs from the other by 5% in each direction, for example.

According to another advantageous embodiment, provision is made for the incising ridge to arrive at a crossing of the central fossa and the transverse fossa in the intercuspidation position, which is provided in the case of the molars. The central and transverse fossae permit good removal of food remnants and subsequent wetting with saliva, whereas it is favorable that in the quadrants that are formed by the fossae, arcuate protrusions extend to the ridge in each case that function as convex arcuate areas, to which, in each case, concave arcuate areas may be adjacent.

The formation of two sulci opposite one another, as they are provided in particular, on the first molars of the upper jaw, also serve to promote the asymmetrical structure of the dentures, but so, too, for example, does the mesial or distal shifting of the lingual or buccal ridge of the first pre-molars of the upper jaw. This shifting is particularly beneficial to the laterotrusion, because the ridge of the pre-molars of the lower jaw can move obliquely toward the lateral interior or exterior, without colliding with the ridge of the upper jaw to too great an extent.

This also holds true for the shifted position of the lingual ridges of the molars of the upper jaw across from the buccal ridges toward the periphery of the tooth, which render a free laterotrusion motion possible.

According to the invention, provision is made so that across the entire occlusion surface, concave and convex areas alternate with one another, which promotes free, harmonic motion.

The latter is also supported by the sagittal torsion of the inclination of the ridge from the first pre-molar as far as the second molar, as a result of which the inclination of the ridge continually decreases, and not only is the helicoidal torsion simulated; rather, the realization of various occlusion concepts is simplified as well.

In an advantageous embodiment, provision is made so that in occlusion position, the incising ridges engage at a definite distance from the edge of the masticating surface of the antagonist. In this way, stress on the periphery of the tooth and the motorial unrest induced as a result, is avoided. The stress may, for example, occur within the median 60% of the mesio-distal length of the masticating surface, to the extent that in the mean, at least 20% distance is maintained between the point of stress and the edge of the masticating surface.

According to the invention, provision is made for a statically localized, lingualized intercuspidation, by means of which the physiological and anatomical, as well as the aesthetic needs can be addressed. In this regard, it is particularly favorable that the distally-arranged sulci of the lower pre-molars permit the intercuspidizing of the lingual ridges of the antagonists of the upper jaw.

As a result of the provision of an incising ridge as the primary ridge on the tooth of the upper jaw, as well as due to the embodiment of a lower jaw antagonist ridge at the mesio-lingual position, the mastication loop can be completed at the arcuate protrusions formed there, and grinding occlusions, as well as tilting, as they occur in the case of guidance surfaces that are arranged outside the central position, which are always to be feared, are certainly avoided.

Further details, advantages, and characteristics result from the description of an embodiment that appears below by virtue of the drawing.

BRIEF DESCRIPTION OF THE DRAWINGS

FIG. 2 shows an occlusal view from above, onto an embodiment example of a second molar of the upper jaw;

FIG. 3 shows an occlusal view from above, onto an embodiment example of a first molar of the upper jaw;

FIG. 4 shows an occlusal view from above, onto an embodiment example of a second pre-molar of the upper jaw;

FIG. 5 shows an occlusal view from above, onto an embodiment example of a first pre-molar of the upper jaw;

FIG. 6 shows an occlusal view from above, onto an embodiment example of a second molar of the lower jaw;

FIG. 7 shows an occlusal view from above, onto an embodiment example of a first molar of the lower jaw;

FIG. 8 shows an occlusal view from above, onto an embodiment example of a second pre-molar of the lower jaw;

FIG. 9 shows an occlusal view from above, onto an embodiment example of a first pre-molar of the lower jaw.

A denture according to the invention, 10, exhibits an upper jaw molar, 12, as well as a lower jaw molar, 14, which can achieve occlusion. Both teeth exhibit masticating surfaces or occlusion surfaces, 16 and 18, that face one another. In the extended representation according to FIG. 1, both teeth are in tripodized intercuspidation, in which convex areas, 20, 22, of the occlusion surface, 18, come into contact with an incising ridge 24 of the upper jaw molar, 12, which is present in the lingualized position. The stippled representation of the upper jaw molar, 12, is intended to show the inter-coronal free space clearly.

Figure 1:
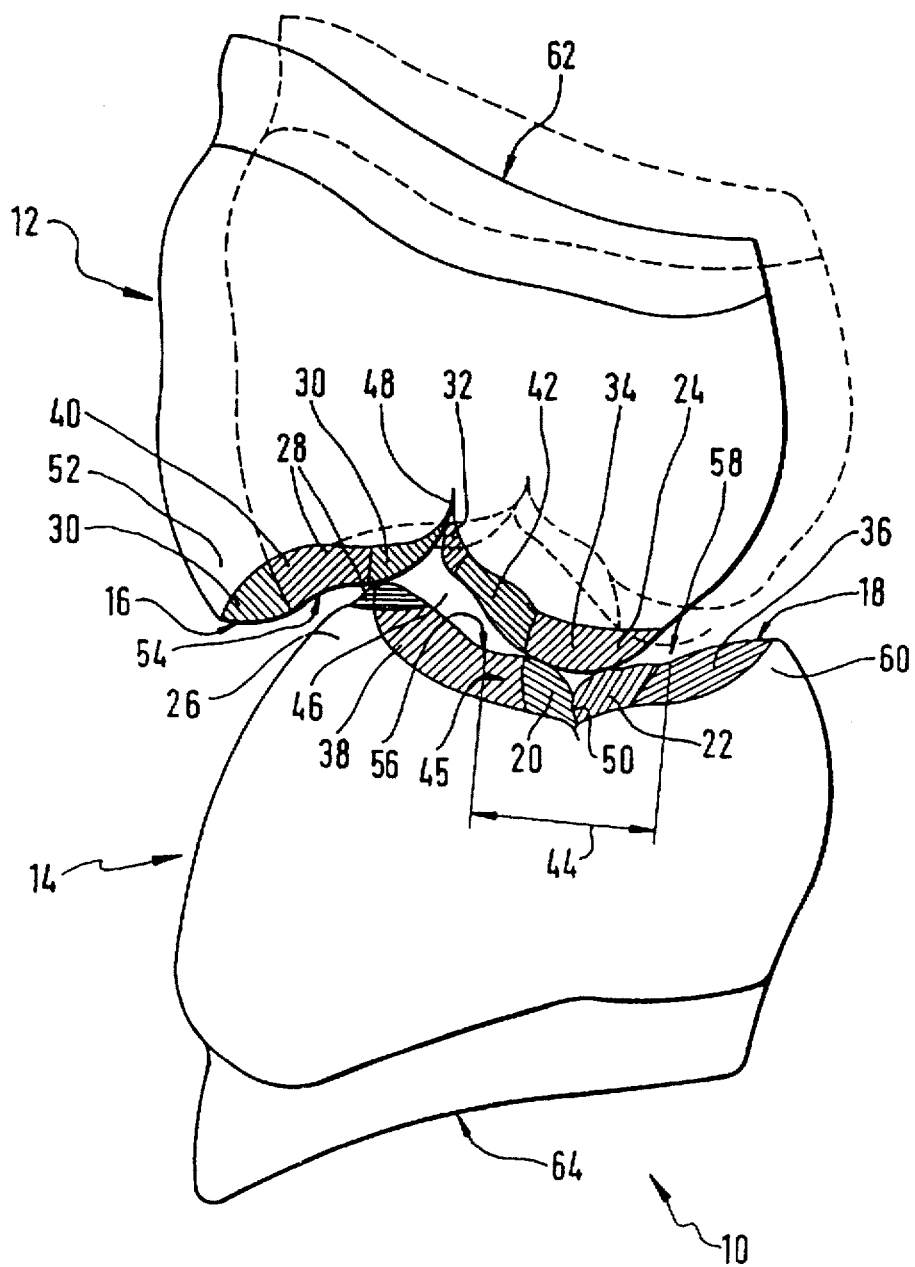
FIG. 1 shows a somewhat schematic representation of a section through an arrangement of molars according to the invention in a denture according to the invention, which are in tripodized intercuspidation.

In the embodiment depicted in FIG. 1, in tripodized intercuspidation, the occlusion surface 18, in buccal position, also comes into contact with the occlusion surface 16, namely at a buccal ridge, 26, across from a lingually inclined oblique surface of the occlusional surface, 16, on the upper jaw molar, 12.

As FIG. 1 shows, convex areas, 20, 22, 28 on the lower jaw molar, 14, as well as convex areas, 30, 32, 34, on the upper jaw molar 12, are interchanged with concave areas, 36, 38 on the lower jaw molar, 14, as well as concave areas, 40, 42, on the upper jaw molar, 12. As a result of this, areas of movement extend laterally from the tripodized intercuspidation, as they are indicated on the lower jaw molar, 14, with the area of movement, 44, and an inter-coronal free space, 46, results.

The area of movement, 44, together with the concave areas that adjoin it, 36 and 38, but solely the buccal and lingual ridges 26 and 60, form, in practical terms, a sulcus, 45 for the incising ridge, 24.

As FIG. 1 shows, in the tripodized intercuspidation, a central fossa, 48, of the upper jaw molar, 12, and a central fossa, 50 of the lower jaw molar, 14, are kept at a distance from each other. The occlusion surface, 18, of the lower jaw molars, 14, toward the buccal side, extends relatively far, however, so that the buccal ridge, 26, on the opposite flank, or an arcuate projection of the buccal ridge, 52, of the molar in the upper jaw, there make contact.

It will be understood that the concave arcuate depressions 54, on the upper jaw molar, 12, as well as the depressions 56 and 58 on the lower jaw molar, 14, need not each be provided in the same plane as the convex areas, 30, 32, or 20 and 22, respectively. For reasons of simplified graphic representation, this is provided in this way here, whereas, according to an advantageous embodiment, provision is made to embody the arcuate depressions 54 through 58 shifted in the drawing plane, so that the inter-coronal free space, 46, also covers a latero-trusion movement, and is present not only in a bucco-lingual direction.

Preferably, the inter-coronal free space, 46, extends primarily in the direction of the mastication loop as it approaches the position of occlusion, to a limited degree, however, oblique to the latter.

In the representation according to FIG. 1, furthermore, the buccal ridge, 26, of the lower jaw molar, 14, and the lingual ridge, 60, of the lower jaw molar, 14, are presented in one plane of the drawing, just as are the corresponding buccal ridge, 52, and the incising ridge, 24, of the upper jaw molar, 12. In the preferred embodiment example, however, the incising ridge, 24, is shifted somewhat toward the distal, which is also beneficial to the latero-trusion.

It will be understood, furthermore, that the representation according to FIG. 1, pertains in each case, to the mesial ridge and sulci. According to the invention, preferably, the molars exhibit preferably, in addition, distal ridges, each of which is separated by a more or less pronounced transverse fossa, 70, from the mesial ridges, and protrude, in a less pronounced manner toward the antagonist than the latter. As a result of this measure, it is possible to realize a graduated masticatory function that ensures that in the case of slight requisite masticatory pressure, the entire masticating surface is available to reduce soft foods, whereas, when the grinding and cutting functions are called for, primarily the incising ridge can work on the antagonist, and this may be accomplished, in addition, in a position of balanced occlusion.

According to a particularly preferred embodiment, provision is made for basal surfaces 62 and 64 to be permitted to extend in a substantially straight manner, in an angle of about 70° to the horizontal. This is beneficial to the computer-supported setting-up of the teeth.

The width of the masticating surface of the lower jaw molar, 14, which extends from the apex of the buccal ridge, 26, to the apex of the lingual ridge, 60, is, in the instance of the embodiment depicted here, 6.5 mm, from which, approximately, the measurements of the teeth of the present embodiment may be derived.

The embodiment of the masticating surface, 16, of the second upper jaw molar, 12, may be seen in FIG. 2. At the mesio-lingual position, the molar exhibits the solidly embodied incising ridge, 24, which, in the case of the representation according to FIG. 2, is arranged at the lower right, and, at mesio-buccal position, the ridge, 52, which is, preferably, embodied in a rather solid fashion.

Retiring, by contrast, at disto-buccal position, are a ridge, 66, and, even more withdrawn at the disto-lingual position, a ridge, 68, is provided.

FIG. 2 shows that a central fossa, 50, is provided, which does not, however, extend in a straight line, but is shifted, rather at mesial position, opposite the distal position, toward the buccal. This corresponds to the shifting of the ridges 24, 52, 66, and 68 toward one another, which, with reference to the apices in each case, nearly describe a parallelogram, whereas the corresponding ridges of the lower jaw, which are visible from FIG. 6, describe, with their apices, a rectangle.

In addition, the central fossa, 50, branches, in the region between the ridge 68 and the ridge 24, to a transverse fossa, 70, which finds its continuation in the region between the ridge 52 and the ridge 66. According to this embodiment, the central fossa 50 and the transverse fossa 70 overlap in the branch that extends between the ridges 24 and 66.

No completely flat and smooth surfaces are provided next to the fossae and ridges that are shown, but rather, arcuate protrusions, sulci and strips, from which an arcuate projection 72 and an arcuate projection 73 are particularly pronounced.

The corresponding embodiment of the first upper jaw molar is visible from FIG. 3. The reference symbols that are used here correspond to those according to FIG. 2. Here, too, the central fossa 50 and transverse fossa, 70, exhibit the lateral shift, in keeping with the shift of the ridges 52, 66, 24, and 68 with reference to one another. From FIG. 2 and FIG. 3, it is possible to see that at the crossing point of the central fossa 50, or rather, the branching off of the transverse fossa, 70, in each case, a sulcus, 74 and 76, is formed. These sulci, too, are shifted toward one another.

Like the second molar of the upper jaw, the first molar of the upper jaw also exhibits a slightly parallelogram-shaped, distorted structure, which engages and can collaborate particularly readily with the nearly square structure of the antagonist on the lower jaw. However, the first molar is preferably longer in mesio-distal direction, by about 2 to 10%, preferably by about 8% and overall, somewhat greater.

In FIGS. 2 and 3, three points, 80, are indicated on the incising ridge, 24, which come to rest upon the corresponding three points in a sulcus of the lower jaw antagonist in tripodized intercuspidation.

FIG. 4 shows how, in the embodiment form that is provided, the second upper jaw pre-molar, 85, may be configured. A central fossa, 50, is provided, which exhibits secondary fossae, 84, which are, however, clearly less conspicuous, and form no more than mortising into the buccal ridge 86 and the lingual ridge, 88.

The central fossa 50 forms practically a kind of axis of symmetry for the second pre-molar in the mesio-distal direction. Taking this central fossa, 50, as a reference point, the buccal ridge, 86, lies obliquely away from the center. By contrast, the lingual ridge, 88, is definitely shifted toward the mesial.

It will be understood that if necessary, the ridge, 86, may be shifted toward the distal, without further ado. As a result of this shifting, the corresponding ridges of the lower jaw antagonists may be more readily moved obliquely for laterotrusion.

A corresponding shift of the ridges, 88, and 86 is also extant in the case of the first pre-molar of the upper jaw, 85, which is shown in FIG. 5.

The second lower jaw molar, 14, which is shown in FIG. 6, exhibits, in addition to the mesial ridges, 26 and 60, distal ridges, 90 and 92, at the buccal or lingual position, respectively. In the case of this tooth, the central fossa, 50, and the transverse fossa, 70, each extend substantially perpendicular to one another, and rather precisely in the middle of the tooth, sulcus, 45, is provided at the crossing of the two aforementioned fossae, 50 and 70, which may engage with the incising ridge, 24, in tripodized intercuspidation at the points 80. It is possible to see that due to the shifting of the ridges in the case of the upper jaw antagonist, 12, not only is there a shift in the mesio-distal direction, but also a shift in the bucco-lingual direction, which facilitates the outward and inward turning of the tooth into the occlusion position.

The first molar of the lower jaw, which is depicted in FIG. 7, exhibits an embodiment that corresponds to that of the second molar of the lower jaw. Here, too, identical parts are represented with identical reference symbols, and the first molar is somewhat larger than the second molar. In addition, the first molar exhibits, at the disto-buccal position, a sulcus, 94, that extends outwardly, which prevents a straight surface that is too long from existing in the mesio-distal direction on the incline of the ridge, 90. Furthermore, the first molar of the lower jaw exhibits three buccal ridges, 26, 90, and 93.

As may be seen from FIG. 7, the lingual ridges, 60 and 92 of the first molar of the lower jaw are rather far removed from one another, so that the transverse fossa, 70, at this position is rather wide. The distances of the apices of the ridges 60 and 92 is greater than the distance of the apices of the buccal ridges, 26 and 90. As a result of this fact, the incising ridge, 24, of the first molar of the upper jaw can move slightly as a result of the transverse fossa 70, without making contact, prematurely with the lingual ridges of the lower jaw, and thus, it cannot prevent the harmonious course of movement.

It will be understood that a corresponding embodiment can also be provided for the second molar of the lower jaw, which is depicted in FIG. 6.

In FIG. 8, the second pre-molar, 95 of the lower jaw is depicted, the position of which is determined by three ridges that lie opposite one another, 87 and 88 lingually, and 86 bucally, which are separated by a central fossa, 50. At points that are removed from one another, transverse sulci, 84, of the central fossa, 50, are provided, which form sulci, 96 and 98, in the areas of their intersection. Provision is made so that the lingual ridge, 88, of the second pre-molar of the upper jaw, comes to rest in the sulcus 96, so that here, too, a good size-reduction effect is possible.

The first pre-molar of the lower jaw, 95, which is depicted in FIG. 9, is embodied, once again in accordance with the pre-molar that is depicted in FIG. 8, and here, too, identical reference symbols refer to identical parts.

Figure 10:
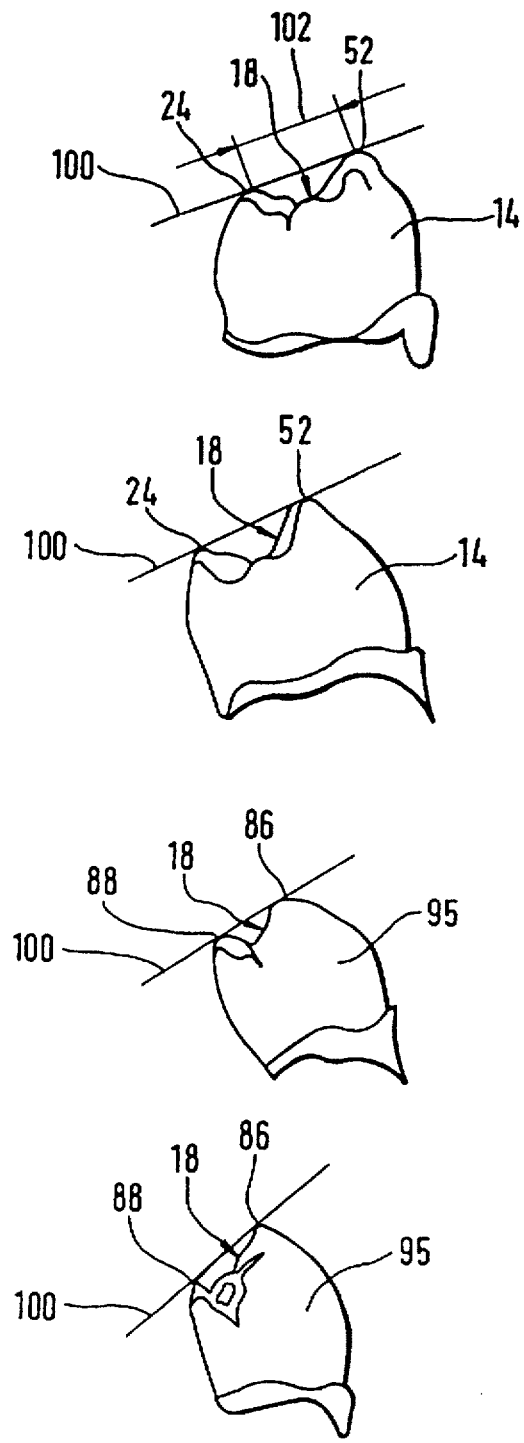
FIG. 10 shows a schematic view of the torsion when assembling a denture according to the invention.

As FIG. 10 shows, the inclination of the ridges of the teeth of the lower jaws varies. In the representation according to FIG. 10, Camper's plain should extend horizontally, and the inclination of the ridges of the first pre-molar, 95, is approximately 40°±3° with reference to Camper's plane. The inclination of the ridges is determined by a straight line, 100, which is laid across the lingual ridge, 88 and the buccal ridge, 86, or, in the case of molars, across the mesio-lingual ridge, 60, and the mesio-buccal ridge, 26. The inclination of the ridge is, in the case of the second pre-molar, 95, which is depicted above the first pre-molar, 95, 33°±3°. In the case of the first molar, 14, which is depicted in FIG. 10 above the second pre-molar, the inclination of the ridge is 27°±3°, and, in the case of the second molar, 14, which is depicted above it, somewhat less.

Accordingly, there is, when viewed in the sagittal direction, a torsion of the masticatory surface, 18, around a sagittal axis. It is also possible to see from FIG. 10 that the width of the masticatory surface, 102, extends in the bucco-lingual direction between the apex of the buccal ridge, 26, and that of the lingual ridge, 60, or between the apices of the distal ridges, 90 and 92.

What is claimed is:

1. A denture made of pre-fabricated teeth comprising: molars (12, 14) for each upper and lower jaw, in which at least each of the upper jaw molars is provided with an incising ridge (24) at lingual position, each of which upper jaw molars, in occlusion position, engages a masticating surface (18) of its lower jaw antagonist, characterized by the fact that the masticating surface (18) of the antagonist (14) exhibits a fossa (45) with at least some convex arcuate areas (20, 22), by means of which the antagonist (14) may be centered in tripodized contact intercuspidation at the incising ridge (24, at 80).

2. A denture according to claim 1 characterized by the fact that concave arcuate areas (36, 38) adjoin the at least in part convex arcuate areas (20, 22) of the antagonist for the purpose of forming an inter-coronal free space (46).

3. A denture according to claim 1, wherein the upper jaw molars have a central fossa (48), and the lower jaw molars have a central fossa (45) and a buccal ridge (26), characterized by the fact that the distance between the central fossa (48) and the lingual ridge (24) of the teeth of the upper jaw

(12) is smaller than the distance between the central fossa (45) and the buccal ridge (26) of the teeth of the lower jaw (14).

4. A denture according claim 1, wherein the lower jaw molars have a central groove (50) and a transverse groove (70), characterized by the fact that the upper jaw's incising ridge (24) engages, in occlusionary position the fossa (45) of the antagonist 14 of the lower jaw, which fossa (45) is formed by the crossing between the central groove (50) and the transverse groove (70).

5. A denture according to claim 1, characterized by the fact that at least one of the upper jaw molars exhibit two sulci (74, 76), one positioned opposite the other, such that one sulcus (76) is provided at the mesio-buccal position, and one sulcus (74) is provided at disto-lingual position, which are connected to one another by means of a central fossa (50), which extends slightly obliquely in a mesio-buccal/ disto-lingual direction, such that from the mesio-buccal sulcus (76) a transverse fossa (70) extends in the buccal direction, and from the disto-lingual sulcus (74), a transverse fossa (70) extends in the lingual direction.

6. A denture according to claim 1, wherein the lower molar are provided with buccal ridges, characterized by the fact that the lingual ridges (92, 60) of the lower jaw molars (14), in comparison with the buccal ridges (90, 26), are shifted toward the edge of the tooth, so that their apices, in the mesio-distal direction are at greater distances from each other than the apices of the buccal ridges (90, 26) of the lower jaw molars (14).

7. A denture according to claim 1, characterized by the fact that ridges (24, 52, 66, 68) of the upper jaw molars (12) approximately describe a parallelogram, whose longest extent extends from the mesio-buccal to the disto-lingual.

8. A denture according to claim 1, characterized by the fact that ridges (26, 60, 90, 92) of the lower jaw molars (14) describe a rectangle with sides of approximately the same length.

9. The denture according to claim 1 wherein the upper molar (12) is further provided with a ridge (52) at buccal position, and wherein the lower molar (14) is provided with ridges (26 and 60) at lingual and buccal positions, characterized by the sides of the ridges (24, 52, 26 and 60) being provided with concave areas (36, 38, 40 and 42), which concave areas are adjacent to at least one convex area (20, 22, 30, 32 and 34), and wherein sulci are provided between the sides of the ridges.

10. A denture made of pre-fabricated teeth comprising: molars and pre-molars for each upper and lower jaw, in which at least the upper jaw molars at lingual position exhibit an incising ridge (24), each of which, in occlusion position, is intended to engage the masticating surface (18) of its lower jaw antagonist in each case, characterized by the fact that the masticating surface (18) of the lower jaw antagonist (14) exhibits a sulcus (45) with at least some convex arcuate areas (20, 22), by means of which the antagonist (14) may be centered in tripodized contact intercuspidation at the incising ridge (24).

11. A denture according to claim 10, wherein at least one of the pre-molars of the lower jaw exhibit two sulci (96, 98), characterized by the fact that one ridge of the antagonist engage the sulci, the pre-molars of the upper jaw exhibit a fossa (50) that extends mesio-distally.

12. A denture according to claim 10, characterized by the fact that at least two pre-molars each exhibit a central fossa (50).

13. A denture according to claim 10, wherein at least one pre-molar of the upper jaw is provided with a lingual ridge (88) and a central fossa, characterized by the fact that the apex of the lingual ridge (88) of a pre-molar of the upper jaw, with reference to the median lateral position of the central fossa (50), is shifted toward the mesial by 5° to 30°.

14. A denture according to claim 10, the first pre-molar of the upper jaw is provided with a buccal ridge and a central fossa, characterized by the fact that the apex of the buccal ridge (86) of the first pre-molar of the upper jaw, with reference to the median lateral position with respect to the central fossa (50) of this tooth is shifted toward the distal by 5° to 30°.

15. A denture according to claim 10 wherein the lower molars and the pre-molars have buccal and lingual ridges, characterized by the fact that in the lower jaw the inclination of the ridges, viewed in sagittal direction, decreases continually from the first pre-molar to the second molar (14) and that the first pre-molar (95) exhibits an inclination of ridge of approximately 40°±3° with reference to Camper's plane, the second pre-molar (95) one of 33°±3°, the first molar (14) one of 27°±3° and the second molar (14) an almost identical, or somewhat flatter inclination of ridge when compared with the first molar (14).

* * * * *